US011202688B2

(12) United States Patent
Lee

(10) Patent No.: US 11,202,688 B2
(45) Date of Patent: Dec. 21, 2021

(54) METHOD OF IMPROVING DUCTILITY OF NEEDLE FOR ROOT CANAL TREATMENT DEVICES AND METHOD OF MANUFACTURING NEEDLE FOR ROOT CANAL TREATMENT DEVICES INCLUDING METHOD OF IMPROVING DUCTILITY OF NEEDLE FOR ROOT CANAL TREATMENT DEVICES

(71) Applicants: B&L BIOTECH, INC., Ansan-si (KR); In Whan Lee, Seoul (KR)

(72) Inventor: In Whan Lee, Seoul (KR)

(73) Assignees: B&L BIOTECH, INC., Ansan-si (KR); In Whan Lee, Seoul (KR)

( * ) Notice: Subject to any disclaimer, the term of this patent is extended or adjusted under 35 U.S.C. 154(b) by 175 days.

(21) Appl. No.: 16/535,293

(22) Filed: Aug. 8, 2019

(65) Prior Publication Data
US 2020/0297456 A1  Sep. 24, 2020

(30) Foreign Application Priority Data
Mar. 22, 2019  (KR) .................. 10-2019-0032901

(51) Int. Cl.
*A61C 5/46* (2017.01)
*B21G 1/00* (2006.01)
(Continued)

(52) U.S. Cl.
CPC ............. *A61C 5/46* (2017.02); *A61C 5/50* (2017.02); *B21G 1/006* (2013.01); *B21G 1/08* (2013.01);
(Continued)

(58) Field of Classification Search
CPC .... A61C 5/46; A61C 5/50; A61C 5/55; A61C 5/40; A61B 2017/00526; C21D 9/26;
(Continued)

(56) References Cited

U.S. PATENT DOCUMENTS 4,993,941 A * 2/1991 Maita ...................... A61C 5/40
433/80
5,533,982 A   7/1996 Rizk et al.
(Continued)

FOREIGN PATENT DOCUMENTS

JP   61-243115 A   10/1986
JP   06-228649 A   8/1994
(Continued)

OTHER PUBLICATIONS

Communication dated May 26, 2020, issued by the Japanese Patent Office in counterpart Japanese Application No. 2019-148108.
(Continued)

*Primary Examiner* — Matthew P Travers
(74) *Attorney, Agent, or Firm* — Sughrue Mion, PLLC

(57) ABSTRACT

The present disclosure relates to a method of manufacturing a needle for root canal treatment devices having improved ductility. The method of the present disclosure includes a step of manufacturing a hollow needle body in a desired shape using an alloy or a single metal, a step of filling the hollow of the needle body with a packing member, a step of heat-treating the needle body at a predetermined temperature under an inert gas atmosphere after the needle body is placed in a vacuum chamber, and a step of cooling and hardening the needle body.

12 Claims, 5 Drawing Sheets

(51) Int. Cl.
*B21G 1/08* (2006.01)
*B23P 15/00* (2006.01)
*A61C 5/50* (2017.01)
*A61B 17/00* (2006.01)
*C21D 9/26* (2006.01)
*A61C 5/55* (2017.01)

(52) U.S. Cl.
CPC ..... *B23P 15/00* (2013.01); *A61B 2017/00526* (2013.01); *A61C 5/55* (2017.02); *C21D 9/26* (2013.01)

(58) Field of Classification Search
CPC .... C22C 9/00; C22C 5/06; C22C 5/08; C23C 30/00; B32B 15/018; B32B 15/01; C22F 1/14; C22F 1/08; B21G 1/006; B21G 1/08; A61M 2207/00
See application file for complete search history.

(56) References Cited

U.S. PATENT DOCUMENTS

| | | | |
|---|---|---|---|
| 5,814,166 | A | 9/1998 | Ackerman et al. |
| 6,343,929 | B1 * | 2/2002 | Fischer .................. A61C 3/005 433/224 |
| 2009/0157116 | A1 | 6/2009 | Cichocki, Jr. et al. |
| 2010/0143862 | A1 * | 6/2010 | Lee .......................... A61C 5/50 433/81 |
| 2011/0271529 | A1 | 11/2011 | Gao et al. |
| 2015/0342714 | A1 * | 12/2015 | Fritze ................... A61C 19/063 433/90 |

FOREIGN PATENT DOCUMENTS

| | | |
|---|---|---|
| JP | 2004-517691 A | 6/2004 |
| JP | 2006-528049 A | 12/2006 |
| KR | 10-2010-0137985 A | 12/2010 |
| KR | 10-2018-0079663 A | 7/2018 |
| WO | 2013/074896 A1 | 5/2013 |
| WO | 2015/104100 A1 | 7/2015 |

OTHER PUBLICATIONS

Communication dated Jul. 16, 2020, issued by the Korean Patent Office in counterpart Korean Application No. 10-2019-0032901.
Communication dated May 29, 2020, issued by the Australian Patent Office in counterpart Australian Application No. 2019208148.
Extended European Search Report dated Mar. 12, 2020, issued by the European Patent Office in counterpart European Patent Application No. 19193405.8.
Fukata Heat Treatment Industry, "Stock quenching (normalizing, annealing), and annealing", online, Aug. 19, 2018, Internet URL:http://www.fukada-net.co.jp/technique/material.php, (4 pages total).
Notice of Reasons for Refusal dated Feb. 2, 2021 from the Japanese Patent office in JP Application No. 2019-148108.

* cited by examiner

METHOD OF IMPROVING DUCTILITY OF NEEDLE FOR ROOT CANAL TREATMENT DEVICES AND METHOD OF MANUFACTURING NEEDLE FOR ROOT CANAL TREATMENT DEVICES INCLUDING METHOD OF IMPROVING DUCTILITY OF NEEDLE FOR ROOT CANAL TREATMENT DEVICES

CROSS-REFERENCE TO RELATED APPLICATION

This application claims priority to Korean Patent Application No. 10-2019-0032901, filed on Mar. 22, 2019 in the Korean Intellectual Property Office, the disclosure of which is incorporated herein by reference.

BACKGROUND OF THE DISCLOSURE

Field of the Disclosure

The present disclosure relates to a method of improving the ductility of a needle for root canal treatment devices and a method of manufacturing a needle for root canal treatment devices including the method of improving the ductility of a needle for root canal treatment devices. More specifically, according to the present disclosure, a needle body having improved ductility may be manufactured through a heat treatment process and a cooling process, and a needle capable of being bent in a desired direction and angle and capable of being repeatedly bent and unfolded may be provided.

Description of the Related Art

In general, when dental pulp, which is the nerve tissue of a tooth, is damaged by severe dental caries or tooth breakage, root canal treatment (endodontic treatment) is performed to restore tooth function. In root canal treatment, damaged dental pulp is removed, and a space formed by removing the dental pulp is filled with a filling material (gutta-percha, which is a natural resin) using a root canal treatment device.

A root canal treatment device includes a body in which a knob is integrally formed, a hollow needle disposed on one side of the body, and a heater for melting a filling material filling the hollow needle. According to this configuration, when the hollow needle is filled with a filling material and the heater is operated, the filling material is melted and discharged from the needle to fill dental pulp.

Meanwhile, a needle detachably attached to the body of a root canal treatment device is manufactured so that a user can bend the needle at a predetermined angle. However, since most of conventional needles are formed of a metal material having high brittleness, it is difficult to change the angle and direction of the needle once bent.

When the needle is forcibly unfolded or bent to change the angle and direction of the needle, the needle may be easily broken due to brittleness thereof. Accordingly, when a conventional needle is used, it is difficult to determine a treatment position. In addition, since a needle in use needs to be replaced with a needle suitable for each treatment position, inconvenience may increase.

SUMMARY OF THE DISCLOSURE

Therefore, the present disclosure has been made in view of the above problems, and it is an object of the present disclosure to provide a method of improving the ductility of a needle for root canal treatment devices and a method of manufacturing a needle for root canal treatment devices including the method of improving the ductility of a needle for root canal treatment devices. According to the present disclosure, a needle body formed of a metal or alloy is subjected to a heat treatment process and a cooling process to improve the ductility of the needle body while maintaining the intrinsic strength thereof. Accordingly, the needle body manufactured according to the method of the present disclosure may be repeatedly bent and unfolded, which may increase the accuracy of treatment and operator convenience.

In accordance with one aspect of the present invention, provided is a method of manufacturing a needle for root canal treatment devices including a step of heat-treating a needle body at a predetermined temperature under an inert gas atmosphere after the needle body is placed in a vacuum chamber and a step of cooling the heat-treated needle body.

According to one embodiment, the method of manufacturing a needle for root canal treatment devices may further include, before the step of heat-treating, a step of manufacturing a hollow needle body in a desired shape using an alloy or a single metal, wherein the step of manufacturing may include a step of filling the hollow of the needle body with a packing member.

According to one embodiment, in the step of manufacturing, the needle body may be formed of one of copper (Cu), silver (Ag), and alloys of copper (Cu) and silver (Ag).

According to one embodiment, in the step of manufacturing, the surface of the needle body may be selectively coated with gold (Au) or silver (Ag).

According to one embodiment, in the step of manufacturing, a deep drawing process may be used to manufacture the needle body.

According to one embodiment, in the step of heat-treating, an internal pressure of the chamber may be adjusted to 10-3 to 1 Torr using a vacuum pump, argon (Ar) may be supplied into the chamber, and then the needle body may be heat-treated for 1 to 10 hours at a temperature of 100 to 900° C. under atmospheric pressure.

According to one embodiment, in the step of cooling, the heat-treated needle body may be allowed to stand for 30 minutes to 5 hours to cool naturally.

According to one embodiment, the method of manufacturing a needle for root canal treatment devices may further include, after the step of cooling, a step of separating a packing member from the needle body and washing the needle body.

In accordance with another aspect of the present invention, provided is a method of improving the ductility of a needle for root canal treatment devices including a step of heat-treating a needle body at a predetermined temperature under an argon (Ar) atmosphere after the needle body is placed in a vacuum chamber.

According to one embodiment, the method of improving the ductility of a needle for root canal treatment devices may further include, before the step of heat-treating, a step of manufacturing a hollow needle body in a desired shape using an alloy or a single metal, wherein the step of manufacturing may include a step of filling the hollow of the needle body with a packing member.

According to one embodiment, in the step of manufacturing, the needle body may be formed of one of copper (Cu), silver (Ag), and alloys of copper (Cu) and silver (Ag).

According to one embodiment, in the step of manufacturing, the surface of the needle body may be selectively coated with gold (Au) or silver (Ag).

According to one embodiment, in the step of heat-treating, an internal pressure of the chamber may be adjusted to $10^{-3}$ to 1 Torr using a vacuum pump, argon (Ar) may be supplied into the chamber, and then the needle body may be heat-treated for 1 to 10 hours at a temperature of 100 to 900° C. under atmospheric pressure.

According to one embodiment, the method of improving the ductility of a needle for root canal treatment devices may further include, after the step of heat-treating, a step of cooling and hardening the needle body, wherein, in the step of cooling, the heat-treated needle body may be allowed to stand for 30 minutes to 5 hours to cool naturally.

DETAILED DESCRIPTION OF THE DISCLOSURE

Figure 1:
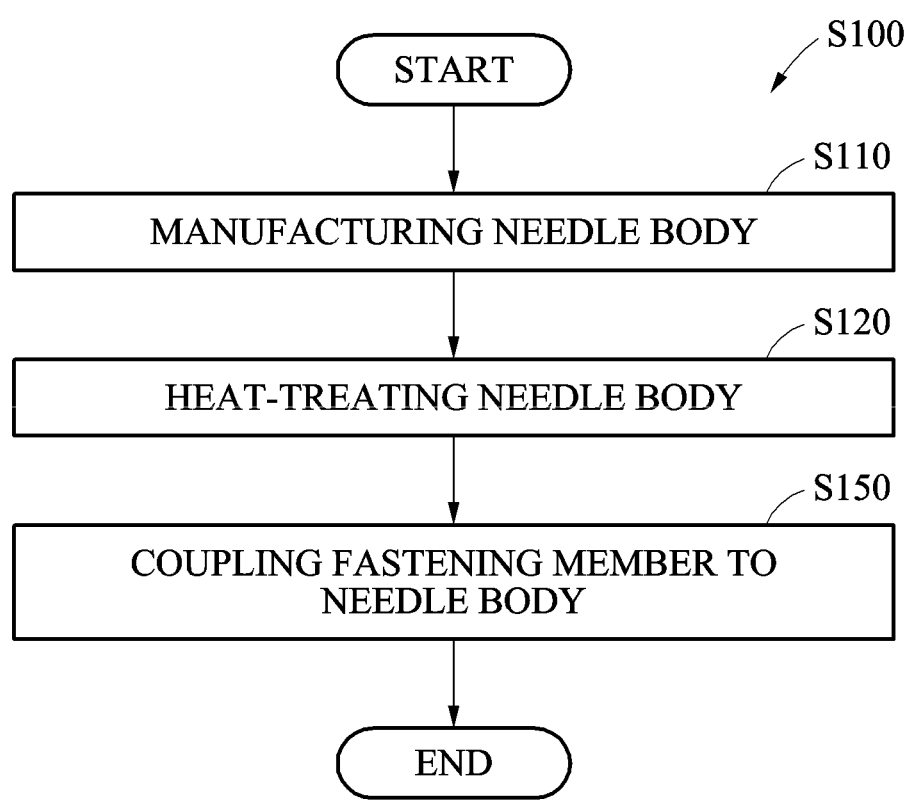
FIG. 1 is a block diagram for explaining a method of manufacturing a needle for root canal treatment devices according to one embodiment of the present disclosure.

Hereinafter, a method of manufacturing a needle for root canal treatment devices according to the present disclosure will be described with reference to the accompanying drawings. Here, the same reference numerals are used for the same components, and repeated description and detailed description of known functions and configurations that may obscure the gist of the present disclosure are omitted. These embodiments are provided to more fully describe the present disclosure to those skilled in the art. Accordingly, the shapes and sizes of the elements in the drawings can be exaggerated for clarity.

Figure 2:
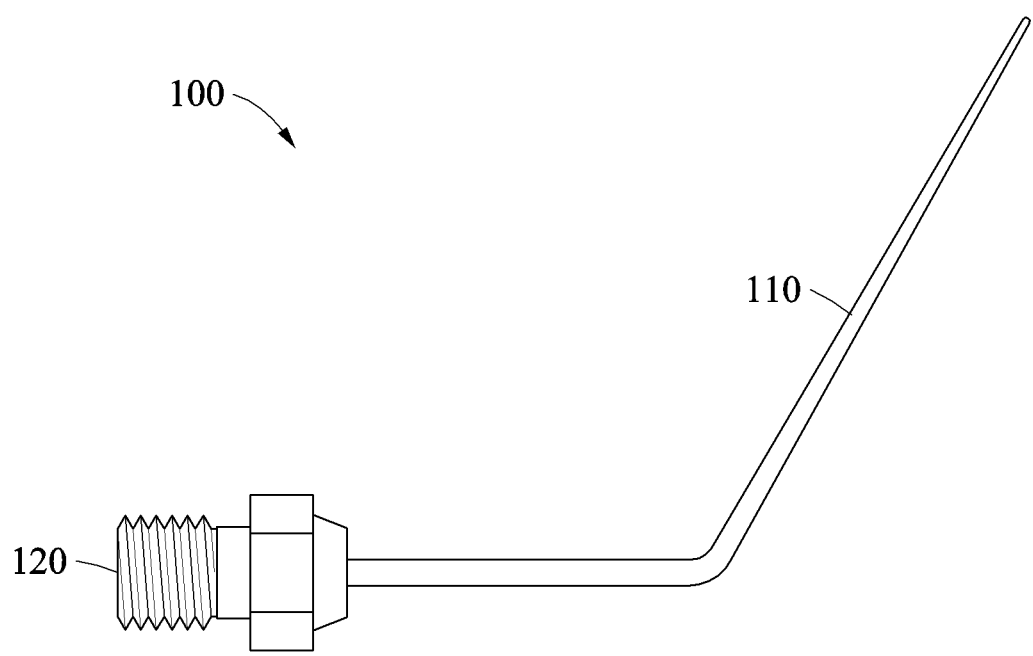
FIG. 2 is a perspective view of the needle for root canal treatment devices manufactured according to the method shown in FIG. 1.
Figure 3:
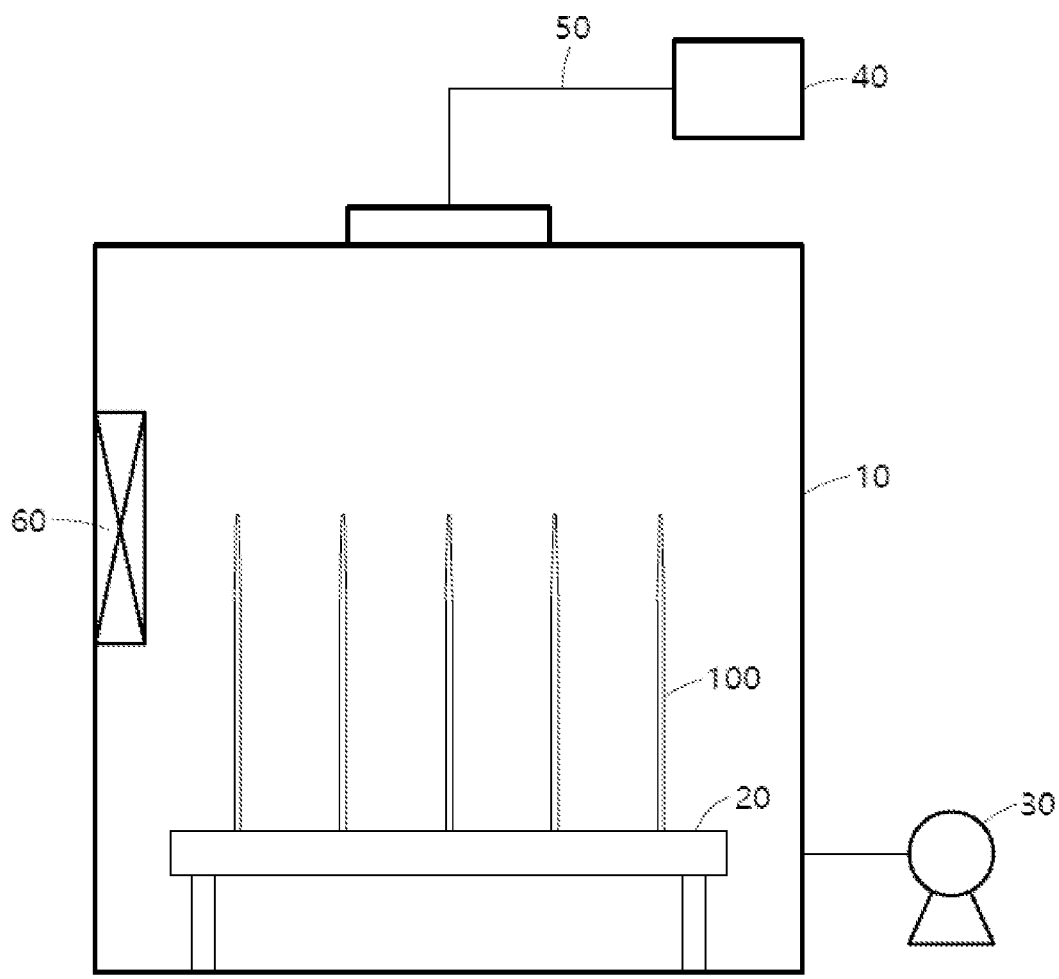
FIG. 3 is a schematic side cross-sectional view of an apparatus for heat-treating the body of the needle for root canal treatment devices.
Figure 4:
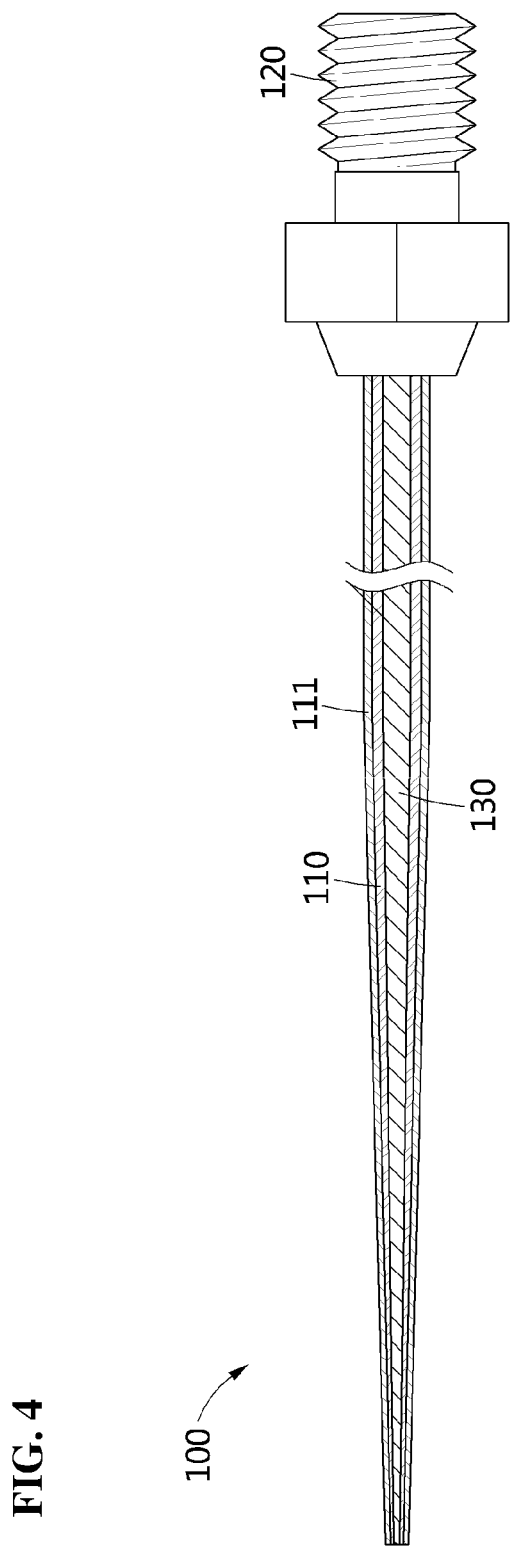
FIG. 4 is a cross-sectional view of the needle for root canal treatment devices having a configuration in which a fastening member is coupled to a needle body.

FIG. 1 is a block diagram for explaining a method of manufacturing a needle for root canal treatment devices according to one embodiment of the present disclosure, FIG. 2 is a perspective view of the needle for root canal treatment devices manufactured according to the method shown in FIG. 1, FIG. 3 is a schematic side cross-sectional view of an apparatus for heat-treating the body of the needle for root canal treatment devices, and FIG. 4 is a cross-sectional view of the needle for root canal treatment devices having a configuration in which a fastening member is coupled to a needle body.

As shown in FIGS. 1 to 4, method S100 of manufacturing a needle for root canal treatment devices includes step S110 of manufacturing a needle body, step S120 of heat-treating the needle body, and step S150 of coupling a fastening member to the needle body.

In step S110, a hollow needle body 110 is manufactured to have a desired shape using an alloy or a single metal. Since a hollow is formed inside the needle body 110, the hollow may be filled with gutta-percha, which is a root canal treatment material.

The needle body 110 may be formed so that, when a solid root canal treatment material is heated by a heater provided in the body of the root canal treatment device, the melted root canal treatment material having a low viscosity is injected into the needle body 110. For example, the needle body 110 may have a straight shape, a stepped shape in which the width of a discharge portion is smaller than the width of an inlet portion, or a tapered shape in which the width of a discharge portion gradually decreases. However, the shape of the needle body 110 is not limited to the above examples, and the needle body 110 may be embodied in various forms.

In step S110, the needle body 110 may be formed through a deep drawing process or a swaging process.

Deep drawing is a process in which the diameter of a product is reduced or the periphery of the inlet of the product is narrowed toward the middle of the product so that the product has a tapered shape. Swaging is a forging process, and refers to a process of longitudinally compressing a material to reduce or increase the cross-section of some or all of a material.

Specifically, the needle body 110 may be formed of one of copper (Cu), silver (Ag), and alloys of copper (Cu) and silver (Ag). To prevent the needle body 110 from being oxidized due to external environments, a coating film 111 may be formed on the surface of the needle body 110 by selectively coating the surface of the needle body 110 with gold (Au) or silver (Ag). In this case, a material forming the needle body 110 and a material coated on the surface of the needle body 110 are preferably different from each other. For example, the needle body 110 may be formed of a single metal such as copper, silver, or an alloy of copper and silver. In addition, the surface of the needle body 110 formed of silver may be coated with silver or gold.

Step S110 may include a step of filling the hollow of the needle body 110 with a packing member 130 (see FIG. 4). This serves to prevent the needle body 110 from being deformed when the needle body 110 is heat-treated in step S120 to be described later. The kind of material forming the packing member 130 is not limited, but the packing member 130 is preferably formed of a material that is not deformed during heat treatment. For example, the packing member 130 may be formed of an elastic silicon material.

The step of filling the needle body 110 with the packing member 130 is not a mandatory step and may be omitted. However, as described above, the step of filling may be additionally performed to prevent the needle body 110 from being deformed when the needle body 110 is heat-treated.

As shown in FIG. 3, in step S120, the needle body 110 is placed in a vacuum chamber 10, and heat treatment is performed at a predetermined temperature under an inert gas atmosphere. In this case, a support 20 may be provided in the chamber 10, and the needle body 110 is vertically placed on the support 20 so that the entire surface of the needle body 110 may be uniformly heat-treated. The number of the needle body 110 to be placed in the chamber 10 is not limited, but the needle bodies 110 are preferably provided in the chamber 10 to improve manufacturing efficiency.

Specifically, in step S120, the internal pressure of the chamber 10 may be adjusted to $10^{-3}$ to 1 Torr using a vacuum pump 30, argon (Ar), which is an inert gas, may be supplied into the chamber 10, and then heat treatment of the needle body 110 may be performed for 1 to 10 hours at a temperature of 100 to 900° C. under atmospheric pressure.

Figure 5:
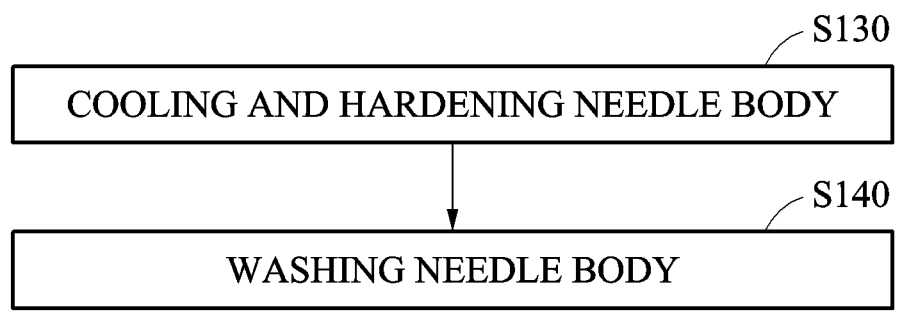
FIG. 5 is a block diagram for explaining additional steps included in the method of manufacturing a needle for root canal treatment devices according to one embodiment of the present disclosure shown in FIG. 1.

As shown in FIG. 5, method S100 according to one embodiment may further include step S130 of cooling and hardening the needle body 110 and step S140 of washing the needle body 110.

In step S130, the heat-treated needle body 110 is cooled and hardened. In this case, the needle body 110 is preferably cooled in a natural cooling manner instead of being cooled under a specific cooling atmosphere. For example, the heat-treated needle body 110 is preferably allowed to stand for 30 minutes to 5 hours so as to be naturally cooled.

Since the needle body 110 is cooled in this manner after heat treatment, the ductility of the needle body 110 may be increased without changing the intrinsic strength of a metal, so that the needle body 110 may be bent or unfolded in a desired direction and angle. Accordingly, the needle body 110 may be freely bent according to positions of treatment, increasing the accuracy of treatment and operator convenience.

In addition, when the heat-treated needle body 110 is cooled, gas such as nitrogen may be supplied. That is, in step S130, the heat-treated needle body 110 is naturally cooled at a room temperature, and nitrogen is supplied to lower the temperature of the heat-treated needle body 110 for the next step.

In addition, method S100 may further include step S140 after step S130.

In step S140, the cooled needle body 110 is removed from the chamber 10. Then, the packing member 130 may be separated from the needle body 110, and the needle body 110 may be washed to remove impurities from the surface of the needle body 110. For example, cleaning liquid may be water or an alcohol. The cleaned needle body 110 may be assembled into the main body of the root canal treatment device.

In addition, since, in step S120, heat treatment of the needle body 110 is performed in the vacuum or nitrogen-filled chamber 10, the heat-treated needle body 110 is not contaminated and thus a separate washing process may be unnecessary. Accordingly, depending on heat treatment environments in step S120, step S140 may not be a mandatory process and thus may be omitted.

In step S150, a fastening member 120 coupled to the main body of the root canal treatment device is coupled to one side of the needle body 110. Accordingly, the needle body 110 may be coupled to the main body of the root canal treatment device via the fastening member 120, and may be separated from the main body of the root canal treatment device.

A process of manufacturing a needle 100 for root canal treatment devices will be described with reference to FIGS. 1 to 5.

First, the hollow needle body 110 is manufactured using an alloy or a single metal. In this case, a material forming the needle body 110 is not particularly limited, but copper or a copper alloy having high ductility is preferably used to form the needle body 110 of a desired shape. After the shaping process, the surface of the needle body 110 is preferably coated with gold or silver.

After filling the packing member 130 in the hollow of the manufactured needle body 110, the needle body 110 is placed in the vertical direction on the support 20 provided inside the chamber 10. In this case, to remove impurities inside the chamber 10, vacuum may be formed by adjusting an internal pressure to $10^{-3}$ to 1 Torr. For this purpose, the vacuum pump 30 for adjusting pressure may be connected to one side of the chamber 10.

In addition, a gas supply pipe 50 connected to a gas supply 40 is provided at one side of the chamber 10 to supply argon (Ar), which is an inert gas, into the chamber 10. Since the inert gas is supplied from the gas supply 40, chemical reaction that may occur in the needle body 110 may be suppressed and the internal pressure of the chamber 10 may be maintained at atmospheric pressure.

In this state, the needle body 110 is heat-treated at a temperature of 100 to 900° C., preferably 650° C., for about one hour using a heating member 60 provided inside the chamber 10. In this case, when heat treatment temperature is less than 100° C., time required for heat treatment of the needle body 110 is prolonged, which lowers heat treatment efficiency. When heat treatment temperature exceeds 900° C., the needle body 110 may be melted and deformed.

After heat treatment, the needle body 110 is allowed to stand for about 30 minutes to 5 hours to cool naturally. Then, residual heat inside the chamber 10 causes the needle body 110 to gradually cool and harden. After natural cooling is completed, the needle body 110 is removed from the chamber 10, and the packing member 130 is separated from the needle body 110. Then, when necessary, washing is performed to remove impurities adhering to the surface of the needle body 110.

Since the needle body 110 formed through the above described processes has high ductility while maintaining the intrinsic strength of a metal, as shown in FIG. 2, the needle body 110 may be bent or unfolded in a desired angle and direction.

As described above, since the ductility of the needle body 110 manufactured by method S100 is increased by a heat treatment process and a cooling process, the needle body 110 is not easily broken even when the needle body 110 is repeatedly bent or unfolded.

In addition, since the needle body 110 may be bent or unfolded in a desired direction and angle, dental treatment may be performed at a desired position, and thus the accuracy of treatment may be increased. In addition, operator convenience may be improved.

According to the present disclosure, since a needle body is manufactured through a heat treatment process and a cooling process, the ductility of the needle body can be increased, and thus the needle body is not easily broken even when the needle body is repeatedly bent or unfolded.

In addition, since the needle body can be bent or unfolded in a desired direction and angle, dental treatment can be performed at a desired position, and thus the accuracy of treatment can be increased. Also, operator convenience can be improved.

Although the present disclosure has been described through limited examples and figures, the present disclosure is not intended to be limited to the examples. Those skilled in the art will appreciate that various modifications, additions, and substitutions are possible, without departing from the scope and spirit of the disclosure. Therefore, the scope of protection of the present disclosure should be determined only by the appended claims.

DESCRIPTION OF SYMBOLS

110: NEEDLE BODY
111: COATING FILM
120: FASTENING MEMBER
130: PACKING MEMBER

What is claimed is:

1. A method of manufacturing a needle for root canal treatment devices, comprising:

heat-treating a needle body at a predetermined temperature under an inert gas atmosphere after the needle body is placed in a vacuum chamber; and cooling the heat-treated needle body, wherein the method further comprises, before the heat-treating, manufacturing a hollow needle body in a desired shape using an alloy or a single metal, and wherein the manufacturing of the hollow needle body comprises filling a hollow of the needle body with a packing member.

2. The method according to claim 1, wherein, in the manufacturing of the hollow needle body, the needle body is formed of one of copper (Cu), silver (Ag), and alloys of copper (Cu) and silver (Ag).

3. The method according to claim 2, wherein, in the manufacturing of the hollow needle body, a surface of the needle body is selectively coated with gold (Au) or silver (Ag).

4. The method according to claim 1, wherein, in the manufacturing of the hollow needle body, a deep drawing process is used to manufacture the needle body.

5. The method according to claim 1, wherein, in the heat-treating, an internal pressure of the chamber is adjusted to $10^{-3}$ to 1 Torr using a vacuum pump, argon (Ar) is supplied into the chamber, and then the needle body is heat-treated for 1 to 10 hours at a temperature of 100 to 900° C. under atmospheric pressure.

6. The method according to claim 1, wherein, in the cooling, the heat-treated needle body is allowed to stand for 30 minutes to 5 hours to cool naturally.

7. The method according to claim 1, wherein the method further comprises, after the cooling, separating the packing member from the needle body and washing the needle body.

8. A method of improving ductility of a needle for root canal treatment devices, comprising heat-treating a needle body at a predetermined temperature under an argon (Ar) atmosphere after the needle body is placed in a vacuum chamber, wherein the method further comprises, before the heat-treating, manufacturing a hollow needle body in a desired shape using an alloy or a single metal, and wherein the manufacturing comprises filling a hollow of the needle body with a packing member.

9. The method according to claim 8, wherein, in the manufacturing, the needle body is formed of one of copper (Cu), silver (Ag), and alloys of copper (Cu) and silver (Ag).

10. The method according to claim 9, wherein, in the manufacturing, a surface of the needle body is selectively coated with gold (Au) or silver (Ag).

11. The method according to claim 8, wherein, in the heat-treating, an internal pressure of the chamber is adjusted to $10^{-3}$ to 1 Torr using a vacuum pump, argon (Ar) is supplied into the chamber, and then the needle body is heat-treated for 1 to 10 hours at a temperature of 100 to 900° C. under atmospheric pressure.

12. The method according to claim 8, wherein the method further comprises, after the heat-treating, cooling and hardening the needle body, wherein, in the cooling and hardening, the heat-treated needle body is allowed to stand for 30 minutes to 5 hours to cool naturally.

* * * * *